United States Patent [19]

Parchinski

[11] Patent Number: 4,650,491
[45] Date of Patent: Mar. 17, 1987

[54] LOCKING MECHANISM FOR PROSTHESIS COMPONENTS

[75] Inventor: Thomas J. Parchinski, Wanaque, N.J.

[73] Assignee: Pfizer Hospital Products Group, Inc., New York, N.Y.

[21] Appl. No.: 829,264

[22] Filed: Feb. 14, 1986

[51] Int. Cl.⁴ .................... A61F 2/34; F16C 11/06
[52] U.S. Cl. ...................... 623/22; 623/18; 403/140
[58] Field of Search .............. 623/16, 18, 19, 20, 623/21, 22, 23; 403/122, 140, 135

[56] References Cited

U.S. PATENT DOCUMENTS

| | | | |
|---|---|---|---|
| 3,241,226 | 3/1966 | Jorgji | 403/122 |
| 3,863,273 | 2/1975 | Averill | 623/16 |
| 4,051,559 | 10/1977 | Pifferi | 623/22 |
| 4,172,296 | 10/1979 | D'Errico | 623/22 |
| 4,231,120 | 11/1980 | Day | 623/21 |
| 4,408,360 | 10/1983 | Keller | 623/23 |
| 4,564,307 | 1/1986 | Ito | 403/140 |
| 4,577,989 | 3/1986 | Ito | 403/140 |
| 4,596,586 | 6/1986 | Weil | 623/22 |

FOREIGN PATENT DOCUMENTS

| | | | |
|---|---|---|---|
| 0137664 | 4/1985 | European Pat. Off. | 623/22 |
| 0046218 | 3/1983 | Japan | 403/122 |

Primary Examiner—Richard J. Apley
Assistant Examiner—David J. Isabella
Attorney, Agent, or Firm—Charles J. Knuth; Peter C. Richardson; Harold W. Ordway

[57] ABSTRACT

A socket insert component of an acetabular cup prosthesis is held securely within its support shell by a locking mechanism comprising a circumferential groove in the shell concavity perpendicular to the longitudinal axis of the concavity, a first circumferential rib on the outer surface of the insert congruent with the groove, and a second circumferential rib on the outer surface of the insert parallel to and proximate the first rib, the first rib snapping into the groove and the second rib being deformed and pressed against the concavity when the insert and shell are assembled.

5 Claims, 5 Drawing Figures

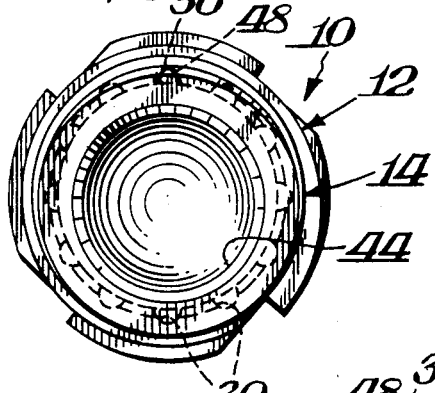
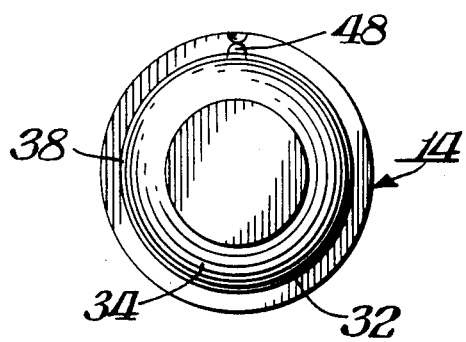
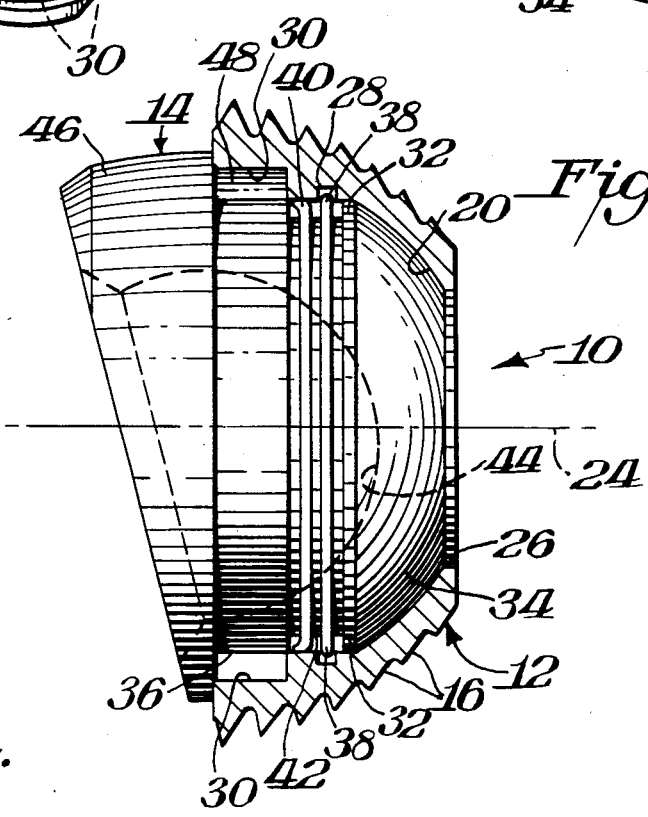
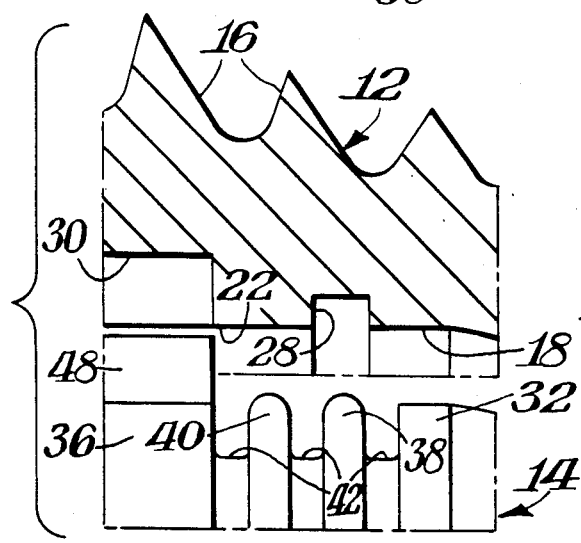
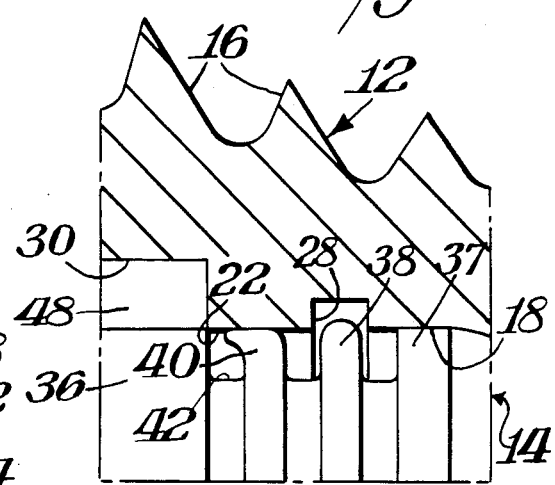

LOCKING MECHANISM FOR PROSTHESIS COMPONENTS

BACKGROUND OF THE INVENTION

The present invention concerns a locking mechanism for securely engaging two components of a bone prosthesis, such as a plastic socket insert within a metal support shell of an acetabular cup prosthesis.

Present day acetabular prostheses often comprise the combination of a plastic cup adapted for receiving a femoral head nestled within a metallic support shell adapted for implantation in the acetabulum. Various means have been provided for receiving the cup within the shell. For example, in U.S. Pat. No. 4,172,296, detent means on the inner surface of the shell engage an annular groove on the outer surface of the cup to permanently affix the cup within the shell; with such means, however, disassembly of the two components is impossible without destruction of the insert. In U.S. Pat. Nos. 3,863,273, 4,051,559 and 4,408,360, an annular protusion or tab on the outer surface of the insert snaps into an annular groove in the inside surface of the shell to hold the cup within the shell. Such designs, however, allow some axial and rotational movement of the cup within the shell. A need therefore still exists, and it is the primary object of the present invention to provide, for a mechanism for joining such components which eliminates their relative axial and rotational movement in the assembled prosthesis but permits its disassembly without damage to the components.

U.S. Pat. No. 4,231,120 discloses a nonrigid orthopedic component secured in cancellous bone by flexible ribs on the component producing an interference fit upon insertion of the component into a substantially complementary but slightly undersized recess in the bone.

SUMMARY OF THE INVENTION

In accordance with the present invention, a bone prosthesis comprises a first component with a concavity having a longitudinal axis; a second component of deformable material having an outer surface that nests within the concavity of the first component; and locking means for securely locking the second component within the first component, the locking means comprising a circumferential groove in the first component concavity lying in a plane perpendicular to the longitudinal axis of the concavity; a first circumferential rib on the outer surface of the second component congruent with the groove in the concavity which snaps into the groove when the second component is fully inserted into the first component; and a second circumferential rib on the outer surface of the second component parallel to and proximate the first circumferential rib, the second rib being deformed and pressed against the concavity when the first and second components are assembled whereby both axial movement and rotational movement between the components are restricted.

In preferred embodiments of the prosthesis, the circumferential groove and ribs are circular, and the surface of the second component includes a substantially parallel groove on either side of each of the first and second ribs to improve the flexibility of the ribs.

The prosthesis may be in the form of an acetabular cup wherein the first component is a support shell for introduction into an acetabulum and the second component is a socket insert for receiving a femoral head. In such a prosthesis, the support shell is preferably constructed of metal and the socket insert of ultra high molecular weight polyethylene.

BRIEF DESCRIPTION OF THE DRAWINGS

The above and other objects, features and advantages of the present invention will be apparent from the appended detailed description of an embodiment thereof in conjunction with the accompanying drawings wherein like reference numerals indicate like structures throughout the several views.

FIG. 1 is a front elevational view of an assembled acetabular cup prosthesis employing the locking means of the present invention;

FIG. 2 is a rear elevational view of the socket insert component of the prosthesis shown in FIG. 1;

FIG. 3 is an enlarged side elevational view of the prosthesis of FIG. 1 shown partly in cross section;

FIG. 4 is an exploded fragmental cross-sectional view of the shell and insert of the prosthesis of FIG. 1 with the insert shown in elevation; and FIG. 5 is a fragmental cross-sectional assembly view of the prosthesis of FIG. 1 showing the insert engaged within the shell.

DESCRIPTION OF THE PREFERRED EMBODIMENT

FIGS. 1 and 3 depict an implantable acetabular cup prosthesis embodying the principles of the present invention and designated generally by reference numeral 10.

Prosthesis 10 comprises a first component or support shell 12 and a second component or socket insert 14 which on assembly rests securely within shell 12.

Shell 12 is fabricated from a biocompatible metal such as titanium, and is of a low-profile, hemispherical design. The outer surface of shell 12 includes a self-tapping thread 16 which allows prosthesis 10 to be inserted into an acetabulum (not shown) without the use of bone cement. The inner surface or concavity 18 of shell 12 is in the form of a spherical portion 20 connected to a cylindrical portion 22 with a common longitudinal axis 24, the polar region of shell 12 being removed to provide a large circular opening 26 for allowing visual assessment of bone apposition during insertion of shell 12 into the acetabulum. Cylindrical portion 22 of concavity 18 is provided with an annular circumferential groove 28 which lies in a plane perpendicular to longitudinal axis 24. Groove 28 has a width of about 45 mils (1.1 mm) and a depth of about 25 mils (0.6 mm). Cylindrical portion 22 is also provided with a series of semi-cylindrical depressions 30 at its distal end for use in orienting insert 14 radially within shell 12.

Insert 14, as shown in FIG. 2, is fabricated from a deformable biocompatible material such as ultra high molecular weight polyethylene (UHMWPE). The outer surface 32 of insert 14 upon assembly nests within concavity 18 of shell 12 and therefore has a spherical portion 34 and cylindrical portion 36, the polar region of spherical portion 34 being removed to be level with opening 26 when assembled.

Cylindrical portion 36, as shown in FIG. 4, has a first annular circumferential rib 38 congruent with groove 28, and a second annular circumferential rib 40 parallel to and proximate rib 38. Ribs 38 and 40 are preferably the same size, with a width of about 35 mils (0.9 mm) and a height above cylindrical portion 36 of about 5 to 8 mils (0.13 to 0.20 mm), and are spaced not less than about 30 mils (0.8 mm) and not more than about 200 mils (5.1 mm) from each other. An annular groove 42 on either side and substantially parallel to each of ribs 38 and 40 having a width of about 30 mils (0.8 mm) and depth of about 50 mils (1.3 mm) imparts a greater flexibility to the ribs 38, 40. Thus, when insert 14 is fully assembled within shell 12 as shown in FIG. 5, rib 38 snaps into groove 28 while rib 40 is deformed or flexed and pressed against concavity 18. This latter interference action insures a positive resistance to axial movement or chatter of insert 14 within shell 12 which the combination of rib 38 within groove 28 alone cannot provide. This interference action of rib 40 against concavity 18 also insures positive resistance to rotational chatter of insert 14 within shell 12. A further advantage of this locking means is the ready separation of insert 14 from shell 12 by appropriate instrumentation without damage to either insert 14 or shell 12.

Insert 14 has a hemispherical cavity 44 for receiving the spherical head of a femoral stem prosthesis (not shown) and a hood 46 adjacent cavity 44 having a 15° superior extension. Hood 46 is oriented radially to correct alignment or anatomical deficiencies by means of a semicylindrical projection 48 on cylindrical portion 36 behind and adjacent hood 46 which is congruent with and inserted into one of depressions 30 upon assembly of insert 14 within shell 12. This insertion of projection 48 into depression 30 prevents gross rotational movement between insert 14 and shell 12, any rotational chatter between these components being prevented by the interference action between rib 40 and concavity 18 discussed above.

While the invention has been described in connection with a preferred embodiment, it also includes alternatives, modifications and equivalents within the spirit and scope of the appended claims. Thus, for example, the prosthesis could be that for a shoulder, elbow, knee, wrist or finger as well as hip joint, and the ribs and grooves could be polygonal or oval as well as circular.

I claim:
1. An implantable bone prosthesis, which comprises:
   a first component for introduction into a bone cavity with a concavity having a longitudinal axis;
   a second component of deformable material having means for receiving an articulating member and an outer surface that nests within the concavity of the first component, and
   locking means for securely locking the second component within the first component, the locking means comprising
   a circumferential groove in the first component concavity lying in a plane perpendicular to the longitudinal axis of the concavity,
   a first circumferential rib on the outer surface of the second component congruent with the groove in the concavity which snaps into the groove when the second component is fully inserted into the first component, and
   a second circumferential rib on the outer surface of the second component parallel to and proximate the first circumferential rib, the second rib being deformed and pressed against the concavity when the first and second components are assembled whereby both axial movement and rotational movement between the components are restricted.
2. The prosthesis of claim 1 wherein the groove and ribs are circular.
3. The prosthesis of claim 1 wherein the outer surface of the second component includes a substantially parallel groove on either side of each of the first and second ribs to improve the flexibility of the ribs.
4. The prosthesis of claim 1 in the form of an acetabular cup wherein the first component is a support shell for introduction into an acetabulum and the second component is a socket insert for receiving a femoral head.
5. The prosthesis of claim 4 wherein the support shell is constructed of metal and the socket insert is constructed of ultra high molecular weight polyethylene.

* * * * *